United States Patent
Hälli et al.

(10) Patent No.: US 7,211,229 B2
(45) Date of Patent: May 1, 2007

(54) METHOD AND APPARATUS FOR THE STERILIZATION OF BIOLOGICAL WASTE

(75) Inventors: Riku Hälli, Palma (FI); Juha Mattila, Järvenpää (FI); Teppo Nurminen, Vantaa (FI); Mauri Salmisuo, Tuusula (FI)

(73) Assignee: Steris Europe Inc. Suomen Sivuliike (FI)

( * ) Notice: Subject to any disclaimer, the term of this patent is extended or adjusted under 35 U.S.C. 154(b) by 0 days.

(21) Appl. No.: 10/491,765

(22) PCT Filed: Oct. 7, 2002

(86) PCT No.: PCT/FI02/00784

§ 371 (c)(1),
(2), (4) Date: Aug. 31, 2004

(87) PCT Pub. No.: WO03/031336

PCT Pub. Date: Apr. 17, 2003

(65) Prior Publication Data

US 2005/0002824 A1   Jan. 6, 2005

(30) Foreign Application Priority Data

Oct. 8, 2001   (FI) .................................. 20011952

(51) Int. Cl.
*C02F 11/00* (2006.01)

(52) U.S. Cl. ........................ 422/307; 422/38; 210/742; 210/175

(58) Field of Classification Search .................. 422/1, 422/38, 307; 210/741, 742, 764, 175
See application file for complete search history.

(56) References Cited

U.S. PATENT DOCUMENTS

| | | | | |
|---|---|---|---|---|
| 3,219,579 A | * | 11/1965 | Kranz | 210/600 |
| 3,986,955 A | * | 10/1976 | Plicque | 203/11 |
| 6,521,133 B1 | * | 2/2003 | Roediger | 210/742 |

FOREIGN PATENT DOCUMENTS

| | | |
|---|---|---|
| EP | 0 391 508 | 3/1990 |
| WO | WO 89/03807 | 5/1989 |
| WO | WO 00/57928 | * 10/2000 |

* cited by examiner

*Primary Examiner*—Gladys JP Corcoran
*Assistant Examiner*—Sean E. Conley
(74) *Attorney, Agent, or Firm*—Kusner & Jaffe; Michael A. Centanni

(57) ABSTRACT

Continuous biowaste sterilization process, the operability of which is ensured in such a way that during process startup, extreme conditions possibly coming into question during operation are simulated, i.e. the greatest possible flow rate and the lowest temperature of the feed flow. In the startup stage, a liquid to be sterlized is circulated in the apparatus, until the capacity has been ascertained, whereafter the discharge stream can be conducted to a sewer system. The apparatus according to the invention comprises, in the flow direction of the biowaste-containing liquid, a storage tank, at least one feed pump capable of delivering a constant flow, at least one heating unit, at least one cooling unit, and a circulation circuit for circulating the biowaste-containing liquid through the heating unit, as well as connecting piping and valves. By means of specific piping and valve arrangements it is also ensured that all parts of the apparatus can be sterilized for maintenance purposes.

8 Claims, 1 Drawing Sheet

METHOD AND APPARATUS FOR THE STERILIZATION OF BIOLOGICAL WASTE

Figure 1:
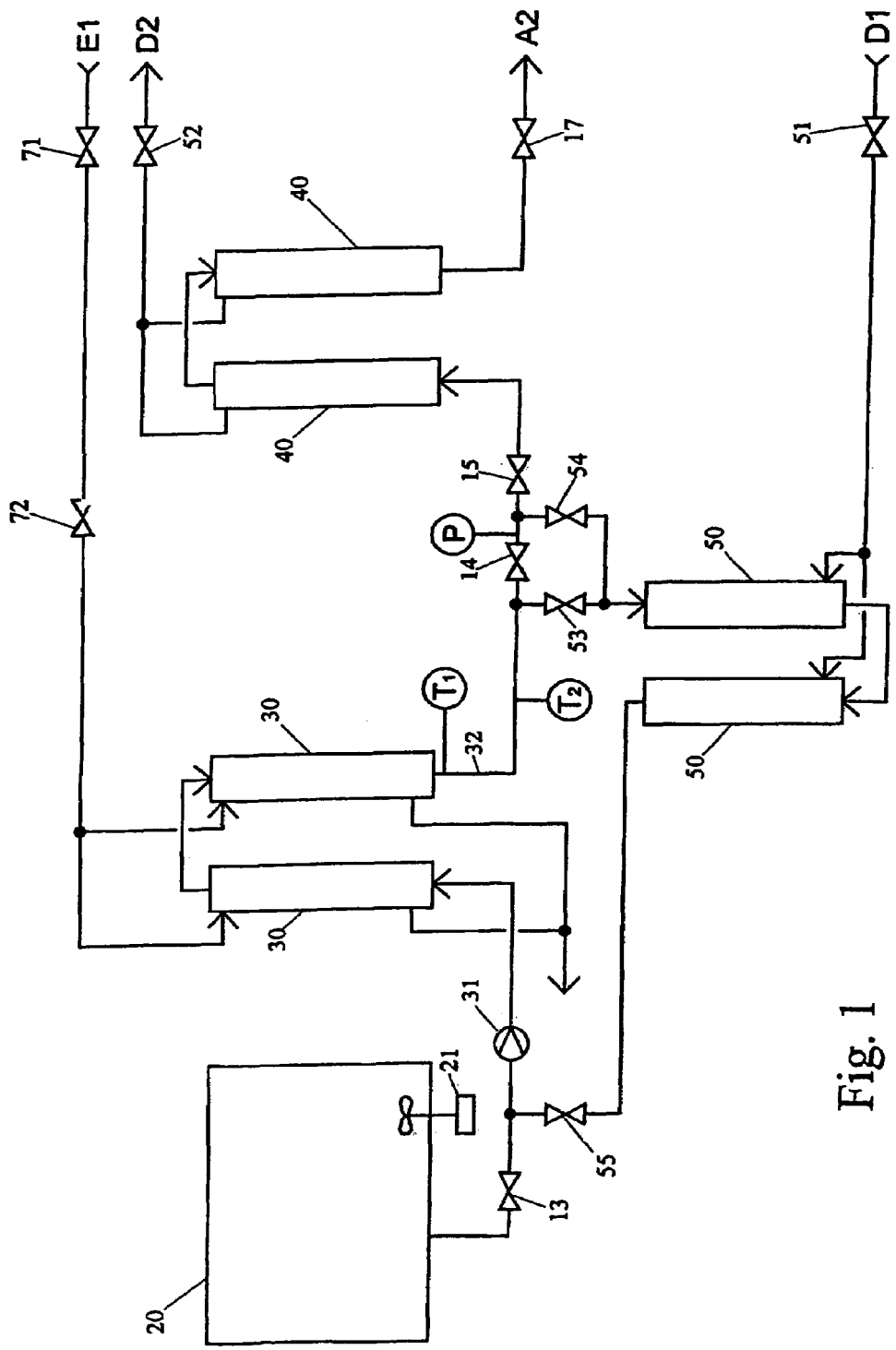

The invention relates to a continuous sterilization process for biological waste and an apparatus for applying said process, the main line of which comprising, in the flow direction of a biowaste-containing liquid, a storage tank, at least one feed pump, at least one heating unit, at least one cooling unit and a circulation circuit for circulating the biowaste-containing liquid through the heating unit, as well as appropriate piping and valves.

Biological waste is produced e.g. in hospitals, agricultural or biological research and production facilities, plasma fractionation facilities, etc. Biological wastes produced in such facilities cannot be directly conducted to a sewer system, as these wastes often contain micro-organisms, such as bacteria, viruses, germs and the like, which are hazardous to humans and animals. Prior to conducting to a sewer system, such biowaste must first be deactivated in a treatment plant designed for this purpose. For the treatment of biowaste, different treatment plants have been designed in which biowaste is sterilized prior to conducting to the sewer system. The sterilization of biowaste can be carried out chemically or by means of heat. The treatment plants can operate continuously or batchwise.

In publication DE 40 16 116, a process is disclosed for the continuous purification of waste waters laden by micro-organisms, such as bacteria, viruses, germs and the like. In said process the waste water is heated to a disinfection temperature by means of a heat exchanger and/or a directly injected hot steam, whereafter the waste water is conducted to a dwell circuit, e.g. to a pressurized vessel. In said dwell circuit, the wastewater is held at the disinfection temperature for a predetermined time. The residence time is measured by injecting an indicator into the wastewater at regular intervals, e.g. every five minutes for 5 seconds, and by measuring the presence of this indicator in the outlet of the dwell circuit. The time difference between indicator injection and detection shows the actual residence time, which can be compared with the residence time setting.

In the journal *Pharmaceutical Engineering*, May/June 2001, pages 70 to 82, an article "Biowaste Systems" by Carl J. Carlson appears, relating to facilities for the treatment of biowaste. The article deals with biowaste treatment facilities of different type as well as with dimensioning principles and problems relating thereto.

According to said article, a typical thermal continuous biowaste sterilisation apparatus comprises a separating unit for solid matter, a storage tank, a heating unit and a dwell circuit as well as a circulation circuit for circulating biowaste through said heating unit and said dwell circuit. According to the article, a typical continuous apparatus comprises the following stages: a heating stage, whereby biowaste is circulated in a heat exchanger and in a dwell circuit, until a temperature sufficient to kill the micro-organisms is reached. This is followed by an operating stage when the biowaste has reached the required temperature over the whole length of the heat exchanger. Thereby the treated biowaste is conducted through cooling equipment to a sewer system. If one or several sterilization parameters (temperature in the dwell circuit, pressure etc.) go outside the predetermined value, and the biowaste is therefore insufficiently sterilized, the process enters a hold state, where the biowaste is circulated through the heating unit and the dwell circuit until the parameter or parameters in question are again within the given limits. In case of an alarm, the apparatus enters the cooling mode, in which the operation of the heating unit is stopped, and the biowaste is recirculated back to the pump feed line until the apparatus is again in working order. According to said article, provisions for the steam sterilization of the parts downstream from the storage tank should be provided, as well as provisions for preventing the transfer of the active biowaste to the cooling circuit. In addition, steam sterilization of the storage tanks the piping, venting filters, etc. should be provided in the apparatus.

The present invention is characterized by the features presented in the characterizing parts of claims 1 and 3.

In the starting up stage of the present heat sterilization process for biowaste, conditions at the upper limits of the capacity thereof, i.e. "worst case" conditions are used. Thereby a liquid is conducted through a heating unit at maximum flow rate, which liquid is subsequently cooled to a level, which corresponds to the lowest defined temperature of the feed flow. When a sufficient sterilization capacity has been reached under these extreme conditions, in other words, when the temperature in the sterilization zone can be maintained at such a high level that it corresponds to the residence time required at the flow rate in question, the process operates with great reliability under all conditions occurring during operation. Preferably, the invention further comprises an arrangement by means of which the tightness of those valves, which are critical during startup and in exceptional situations, can be ensured, and, if necessary, the whole valve system can be sterilized for maintenance measures.

In a process according to the invention, during startup the operability of the process is thus ensured, that at maximum capacity of the pump a liquid flow is conducted through the heating unit, the temperature of which flow has been lowered in the return circuit to a level corresponding to the minimum temperature of the water in the storage tank during operation. The sterilization stage following the heating stage comprises at least measurement of the temperature at the outlet end. When the residence time of the liquid in the sterilization zone has been found sufficient under the above conditions, it can also be assumed that the operability of the process can be maintained independently of variations occurring in the feed.

A device according to the invention is provided with means for verifying the sterilization ability at maxim load during startup. For verifying the capacity of the device, the lowest water temperature and the greatest possible flow are used. In order to ensure that the test actually represents the worst case, the maximum flow must be limited so, that during actual operation it cannot exceed the flow used in the test. Preferably, this is achieved using a positive displacement pump, which at a constant speed of rotation (determined by the electrical motor used) always delivers a constant flow, independent of the pressures at the suction and discharge ends. When a centrifugal pump is used, the maximum flow is limited by setting standards for the suction and discharge pressures and monitoring these values in the control system. Typically, the suction side pressure is essentially constant, because the buffer tank serving as a source is at atmospheric pressure. The discharge back pressure is set to a minimum level, corresponding to the desired maximum flow rate, and the pressure is monitored by means of pressure sensors.

In order to bring the liquid in the return circuit to a temperature corresponding to the minimum temperature of the feed, a heat exchanger and appropriate temperature sensors are provided in the return line. The heat exchanger is dimensioned correspondingly, and minimum limits for cooling water flow and temperature are set in the control system.

A sterilization apparatus according to the present invention comprises a pump capable of a certain maximum flow rate, preferably a displacement pump, by means of which a liquid to be sterilized is conducted through a heating unit at a constant rate. Following the heating unit, a sterilization zone is arranged which is provided with temperature measurement at least at the outlet end. Since the capacity of the pump can be kept constant, it can be ensured that the residence time in the sterilization zone is sufficient to achieve the desired sterilization level. In case the residence time is insufficient, the flow leaving the sterilization zone is conducted through the return circuit back to the heating unit inlet Because the temperature measurement is arranged downstream from the heating unit, it is ensured that the residence time is sufficient.

The return circuit is provided with cooling equipment. When the return circuit is cooled essentially to the minimum temperature occurring in the liquid in the storage tank, it can be ascertained that the temperature of the input flow of the heating unit is not lower than the minimum level required by the heating means.

Preferably, the apparatus according to the invention comprises an arrangement of serial valves arranged after the sterilization zone, by means of which valve arrangement it is ensured that no insufficiently sterilized liquid, which has passed the sterilization zone, can flow outside the apparatus, not even if there is a leakage in a distributing valve.

An advantageous embodiment of the invention is described below with reference to the accompanying drawing.

The FIGURE shows a biowaste treatment apparatus according to the invention. The main components provided in the main line of the treatment apparatus in the flow direction of a biowaste-containing liquid are a storage tank 20, a heating unit 30 and a discharge cooling unit 40. In addition, the treatment apparatus comprises a circulation circuit provided with a circuit cooling unit 50 and connected to the main line, by which circulation circuit the biowaste-containing liquid can be circulated through heating unit 30.

Preferably, the biowaste water is conducted into the storage tank through a solid matter separating unit, which is not shown in the figure. Storage tank 20 is provided with a mixer 21, and a driving motor 22 connected thereto, by which the biowaste water in the storage tank 20 is mixed to prevent sedimentation in the storage tank 20. The storage tank 20 is also provided with a level measurement L.

From the storage tank 20 the biowaste water is conducted into heating unit 30 through an inlet valve 13 of the main line by means of a constant capacity feed pump 31. In this embodiment, heating unit 30 consists of a heat exchanger, in which steam is used as a heat source. After the heating unit, a sterilization zone 32 is arranged, which herein is provided with two temperature measurements T1 and T2. The measurement of the outlet end 12 is essential, because at that point the lowest temperature occurs.

In continuous operation, the sterilized and deactivated biowaste water is conducted from heating unit 30 into a discharge cooling unit 40 via valve group 14 and 15 which forms a barrier site. From discharge cooling unit 40, the deactivated biowaste water is conducted through main line discharge valve 17 to a sewer system at point A2. In this embodiment, discharge cooling unit 40 is a heat exchanger using water as a cooling medium.

In addition to the above-described main line of the treatment apparatus, the apparatus comprises a return circuit beginning at the barrier site of the main line between sterilization zone 32 and discharge cooling unit 40 and ending at the suction inlet of feed pump 31. In front of the first valve 14 of the barrier site of the main line, a first branch is arranged to the first parallel inlet valve 53, and between the first valve 14 and the second valve 15 of the barrier site of the main line, a second outer branch is arranged to a second parallel inlet valve 54. Said serial valves 14 and 15 of the main line and said parallel valves 53, 54 of the circulation circuit together form a barrier site. After said parallel valves 53, 54, the inner branch and outer branch are joined together, whereafter the joined line of the circulation circuit leads to a circuit cooling unit 50 provided in the circulation circuit. After circuit cooling unit 50, the circulation circuit is closed via circuit discharge valve 55 to a point between main line inlet valve 13 and main line feed pump 31. The tightness of the first serial valve 14 can be controlled by means of pressure measurement P coupled to the line between first serial valve 14 and second serial valve 15.

By means of said main line serial valves 14, 15 and said two parallel branches of the circulation circuit, it is ensured that discharge cooling unit 40 and the subsequent zones cannot under any conditions be contaminated.

The cooling water needed in cooling units 40, 50 is brought into circuit cooling unit 50 through cooling water inlet valve 51 at point D1. The cooling water circulated in circuit cooling unit 50 is conducted further to discharge cooling unit 40. The cooling water circulated in discharge cooling unit 40 is discharged via cooling water discharge valve 52 at point D2.

The steam needed in heating unit 30 is fed from point E1 30 through first main steam line inlet valve 71 and second inlet valve 72 into heating unit 30. The condensate formed in heating unit 30 is discharged at point E2.

The startup of the apparatus is carried out by self-testing effected by a control system. Thereafter, biowaste is fed into tank 20, and the circulation of the biowaste is started in beating unit 30 at constant speed by means of the circuit, while the temperature of heating unit 30 is raised to the desired level. The circulating water is cooled in circuit cooling unit storage tank. In this way it is ensured that the load of the heating unit does not exceed its capacity at the beginning of the continuous process.

In the above described startup stage, the integrity of valve 14 is also tested by means of pressure measurement P. If no pressure rise is found by pressure measurement P, valve 14 operates in the desired manner. If as a result of defective tightness of the valve, a pressure rise occurs, it is possible to safely conduct the flow further into the return circuit through the outer branch and valve 53. Thereby valves 14, 15, 53, 54 can be sterilized for maintenance by raising the temperature of the whole circuit to a sufficient level for a sufficient time.

When the measurement of the temperature of the outlet end of the sterilization zone shows that the temperature in the sterilization zone is maintained at a sufficient level relative to the constant flow rate, the circuit can be interrupted by closing valve 53 and opening valve 14, and the deactivated biowaste water can be conducted through discharge cooling means 40 to the sewer system at point A2.

Preferably, the sterilization apparatus shown in the FIGURE is controlled by means of a control system or a computer. Information on the state and operation of all components shown in the FIGURE are fed into the control system, and on the basis of this information the status of the components as well as of the whole apparatus can be shown on a display. In the FIGURE, only the components necessary for understanding the invention are shown, and all other components, e.g. those relating to various measurements, have been left out.

The invention claimed is:

1. A method of sterilizing a biological waste, comprising the steps of:
   a) initiating heating of a heating unit (20);
   b) conveying a waste liquid having an initial temperature from a source through said heating unit (20) at a predetermined rate to heat said waste liquid;
   c) monitoring a temperature (T2) of said waste liquid after said waste liquid passes through said heating unit (20);
   d) comparing said temperature (T2) to a desired sterilization temperature, said temperature (T2) is less than the desired sterilization temperature;
   e) cooling said waste liquid to said initial temperature;
   f) returning said waste liquid at said initial temperature back through said heating unit (20) at said predetermined rate; and
   g) repeating steps c, d, e, and f until said temperature (T2) is greater than or equal to said sterilization temperature.

2. A method of sterilizing a biological waste liquid as defined in claim 1, further comprising the step of:
   h) continuously conveying waste fluid from said source through said heating unit (20) and a first cooling unit (40) to be discharged therefrom when said temperature (T2) is greater than or equal to said sterilization temperature.

3. A method of sterilizing a biological waste liquid as defined in claim 1, wherein the step e) of cooling includes the step of:
   conveying said waste liquid through a second cooling unit (50).

4. An apparatus for the sterilization of a biological waste liquid, comprising:
   a storage tank (20) for storing a waste liquid, wherein said waste liquid has an initial temperature;
   a heating unit (30) for heating said waste liquid disposed downstream of said storage tank (20);
   a sterilization zone (32) disposed downstream of said heating unit (30);
   a pump (31) for conveying a waste liquid from said storage tank (20) along a first flow path through said heating unit (30) and through said sterilization zone (32);
   a first serial valve (14) and a second serial valve (15) disposed in series after said sterilization zone (32) within said first flow path;
   a second flow path beginning downstream of said sterilization zone (32) directing said waste liquid through said heating unit (30) and through said sterilization zone (32);
   at least one means for measuring a temperature of said waste liquid after said heating unit (30);
   a cooling unit (50) disposed within said second flow path for cooling said waste liquid to a predetermined temperature;
   a first branch conduit having a first end fluidly connected to said first flow path between said sterilization zone (32) and said first serial valve (14) and a second end fluidly connected to said cooling unit (50); and
   a first parallel valve disposed within said first branch conduit between said first flow path and said cooling unit (50).

5. An apparatus for the sterilization of a biological waste liquid, comprising:
   a storage tank (20) for storing a waste liquid, wherein said waste liquid has an initial temperature;
   a heating unit (30) for heating said waste liquid disposed downstream of said storage tank (20);
   a sterilization zone (32) disposed downstream of said heating unit (30);
   a pump (31) for conveying a waste liquid from said storage tank (20) along a first flow path through said heating unit (30) and through said sterilization zone (32);
   a first serial valve (14) and a second serial valve (15) disposed in series after said sterilization zone (32) within said first flow path;
   a second flow path beginning downstream of said sterilization zone (32) directing said waste liquid through said heating unit (30) and through said sterilization zone (32);
   at least one means for measuring a temperature of said waste liquid after said heating unit (30);
   a cooling unit (50) disposed within said second flow path for cooling said waste liquid to a predetermined temperature;
   a second branch conduit having a first end fluidly connected to said first flow path between said first serial valve (14) and said second serial valve (15) and a second end fluidly connected to said cooling unit (50); and
   a second parallel valve disposed within said second branch conduit between said first flow path and said cooling unit (50).

6. An apparatus for the sterilization of a biological waste liquid as defined in claims 4 or 5, wherein said predetermined temperature is said initial temperature.

7. An apparatus for the sterilization of a biological waste liquid as defined in claims 4 or 5, wherein said heating unit (30) is a heat exchanger for transferring heat from steam to said waste liquid.

8. An apparatus for the sterilization of a biological waste liquid as defined in claims 4 or 5, wherein means for determining a pressure of said waste liquid is disposed between said first serial valve (14) and said second serial valve (15).

* * * * *